United States Patent
Cerretti

(10) Patent No.: US 7,217,553 B2
(45) Date of Patent: May 15, 2007

(54) NUCLEIC ACIDS ENCODING HUMAN ADAMALYSIN SVPH1-8

(75) Inventor: Douglas P. Cerretti, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 504 days.

(21) Appl. No.: 10/265,125

(22) Filed: Oct. 3, 2002

(65) Prior Publication Data

US 2003/0082771 A1  May 1, 2003

Related U.S. Application Data

(60) Division of application No. 09/617,145, filed on Jul. 14, 2000, now Pat. No. 6,485,956, which is a continuation of application No. PCT/US99/00603, filed on Jan. 12, 1999.

(60) Provisional application No. 60/071,505, filed on Jan. 14, 1998.

(51) Int. Cl.
*C12N 9/00* (2006.01)
*C12N 9/50* (2006.01)
*C07H 21/04* (2006.01)

(52) U.S. Cl. .............. 435/219; 435/4; 435/6; 435/69.1; 435/183; 435/200; 435/252.3; 435/320.1; 435/325; 536/23.2; 536/23.5; 536/23.6; 536/23.7; 530/350

(58) Field of Classification Search .......... 435/4, 435/6, 69.1, 183, 219, 220, 252.3, 320.1; 530/350; 536/23.2
See application file for complete search history.

(56) References Cited

U.S. PATENT DOCUMENTS 5,248,599 A   9/1993 Sakiyama et al.

FOREIGN PATENT DOCUMENTS

GB   9716755.5    10/1997
WO   WO 99/07856   2/1999

OTHER PUBLICATIONS

Perry et al. (Biochem. J. vol. 312:239-244, 1995 and GenBank Accession No. I6525337).*
McKie et al. (Biochem. J. vol. 318:459-462, 1996 and GenBank Accession No. S71949).*
Hooft Van Juijsduijnen, R., "ADAM 20 and 21; two novel human testis-specific membrane metalloproteases with similarity to fertilin-alpha", Gene 206(2): 273-282 (1998).
New England BioLabs Catalog 96/97, "Protein Molecular Weight Markers".
Wolfsberg et al., The Journal of Cell Biology, 131(2):275-278 (1995).
Strausberg, National Cancer Institute, Cancer Genome Anatomy Project, EMBL Database Entry AA758110, Accession No. AA758110, (Jan. 26, 1998), XP002101680.
PubMed Abstract for Hooft Van Juijsduijnen, R., "ADAM 20 and 21; two novel human testis-specific membrane metalloproteases with similarity to fertilin-alpha", Gene 1998 Jan. 12; 206(2):273-82.

* cited by examiner

*Primary Examiner*—Manjunath Rao
(74) *Attorney, Agent, or Firm*—Suzanne A. Sprunger; Susan E. Lingenfelter

(57) ABSTRACT

The disclosure provides purified and isolated SVPH1-8 polypeptides, nucleic acids encoding such polypeptides, processes for production of recombinant forms of such polypeptides, antibodies generated against such polypeptide, and fragmented peptides derived from these polypeptide. In addition, the disclosure provides uses of such polypeptides, fragmented peptides, antibodies and nucleic acids as well as kits containing the foregoing.

14 Claims, No Drawings

NUCLEIC ACIDS ENCODING HUMAN ADAMALYSIN SVPH1-8

CROSS-REFERENCE TO RELATED APPLICATIONS

This application is a divisional application of U.S. Ser. No. 09/617,145, filed Jul. 14, 2000, now U.S. Pat. No. 6,485,956, issued Nov. 26, 2002; which is a continuation of International Application number PCT/US99/00603, filed Jan. 12, 1999, and published in English on Jul. 22, 1999; which claims the benefit of U.S. Provisional Application Ser. No. 60/071,505, filed Jan. 14, 1998; all of which are hereby incorporated by reference.

FIELD OF THE INVENTION

The invention is directed to purified and isolated SVPH1–8 polypeptides, the nucleic acids encoding such polypeptides, processes for production of recombinant forms of such polypeptides, antibodies generated against these polypeptides, fragmented peptides derived from these polypeptides, the use of such polypeptides and fragmented peptides as molecular weight markers, the use of such polypeptides and fragmented peptides as controls for peptide fragmentation, the use of such nucleic acids, polypeptides, and antibodies as cell and tissue markers, and kits comprising these reagents.

BACKGROUND OF THE INVENTION

The discovery and identification of proteins is at the forefront of modern molecular biology and biochemistry. The identification of the primary structure, or sequence, of a sample protein is the culmination of an arduous process of experimentation. In order to identify an unknown sample protein, the investigator can rely upon comparison of the unknown sample protein to known peptides using a variety of techniques known to those skilled in the art. For instance, proteins are routinely analyzed using techniques such as electrophoresis, sedimentation, chromatography, and mass spectrometry.

Comparison of an unknown protein sample to polypeptides of known molecular weight allows a determination of the apparent molecular weight of the unknown protein sample (T. D. Brock and M. T. Madigan, *Biology of Microorganisms* 76–77 (Prentice Hall, 6d ed. 1991)). Protein molecular weight standards are commercially available to assist in the estimation of molecular weights of unknown protein samples (New England Biolabs Inc. Catalog: 130–131, 1995; J. L. Hartley, U.S. Pat. No. 5,449,758). However, the molecular weight standards may not correspond closely enough in size to the unknown sample protein to allow an accurate estimation of apparent molecular weight.

The difficulty in estimation of molecular weight is compounded in the case of proteins that are subjected to fragmentation by chemical or enzymatic means (A. L. Lehninger, *Biochemistry* 106–108 (Worth Books, 2d ed. 1981)). Chemical fragmentation can be achieved by incubation of a protein with a chemical, such as cyanogen bromide, which leads to cleavage of the peptide bond on the carboxyl side of methionine residues (E. Gross, *Methods in Enz.* 11:238–255, 1967). Enzymatic fragmentation of a protein can be achieved by incubation of a protein with a protease that cleaves at multiple amino acid residues (D. W. Cleveland et al., *J. Biol. Chem.* 252:1102–1106, 1977). Enzymatic fragmentation of a protein can also be achieved by incubation of a protein with a protease, such as Achromobacter protease I (F. Sakiyama and A. Nakata, U.S. Pat. No. 5,248,599; T. Masaki et al., *Biochim. Biophys. Acta* 660:44–50, 1981; T. Masaki et al., *Biochim. Biophys. Acta* 660:51–55, 1981), which leads to cleavage of the peptide bond on the carboxyl side of lysine residues. The molecular weights of the fragmented peptides can cover a large range of molecular weights and the peptides can be numerous. Variations in the degree of fragmentation can also be accomplished (D. W. Cleveland et al., *J. Biol. Chem.* 252:1102–1106, 1977).

The unique nature of the composition of a protein with regard to its specific amino acid constituents results in a unique positioning of cleavage sites within the protein. Specific fragmentation of a protein by chemical or enzymatic cleavage results in a unique "peptide fingerprint" (D. W. Cleveland et al., *J. Biol. Chem.* 252:1102–1106, 1977; M. Brown et al., *J. Gen. Virol.* 50:309–316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76–77 (Prentice Hall, 6d ed. 1991)).

When a peptide fingerprint of an unknown protein is obtained, this can be compared to a database of known proteins to assist in the identification of the unknown protein (W. J. Henzel et al., *Proc. Natl. Acad. Sci. USA* 90:5011–5015, 1993; B. Thiede et al., *Electrophoresis* 1996, 17:588–599, 1996). A variety of computer software programs are accessible via the Internet to the skilled artisan for the facilitation of such comparisons, such as Multildent (Internet site: [www.]expasy.ch/sprot/multiident.html), PeptideSearch (Internet site: [www.]mann.embl-heiedelberg. de . . . deSearch/FR_PeptideSearchForm.html), and ProFound (Internet site: [www.]chait-sgi.rockefeller.edu/cgi-bin/prot-id-frag.html). These programs allow the user to specify the cleavage agent and the molecular weights of the fragmented peptides within a designated tolerance. The programs compare these molecular weights to protein databases to assist in the elucidation of the identity of the sample protein. Accurate information concerning the number of fragmented peptides and the precise molecular weight of those peptides is required for accurate identification. Therefore, increasing the accuracy in the determination of the number of fragmented peptides and the precise molecular weight of those peptides should result in enhanced success in the identification of unknown proteins.

Fragmentation of proteins is further employed for the production of fragments for amino acid composition analysis and protein sequencing (P. Matsudiara, *J. Biol. Chem.* 262:10035–10038, 1987; C. Eckerskorn et al., *Electrophoresis* 1988, 9:830–838, 1988), particularly the production of fragments from proteins with a "blocked" N-terminus. In addition, fragmentation of proteins can be used in the preparation of peptides for mass spectrometry (W. J. Henzel et al., *Proc. Natl. Acad. Sci. USA* 90:5011–5015, 1993; B. Thiede et al., *Electrophoresis* 1996, 17:588–599, 1996), for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms* 300–301 (Prentice Hall, 6d ed. 1991)), and for differentiation of homologous proteins (M. Brown et al., *J. Gen. Virol.* 50:309–316, 1980).

In view of the continuing interest in protein research and the elucidation of protein structure and properties, there exists a need in the art for polypeptides suitable for use in peptide fragmentation studies and in molecular weight measurements.

SUMMARY OF THE INVENTION

The invention aids in fulfilling this need in the art. The invention encompasses an isolated nucleic acid molecule comprising the DNA sequence of SEQ ID NO:1 and an isolated nucleic acid molecule encoding the amino acid sequence of SEQ ID NO:2. The invention also encompasses nucleic acid molecules complementary to these sequences. As such, the invention includes double-stranded nucleic acid molecules comprising the DNA sequence of SEQ ID NO:1 and isolated nucleic acid molecules encoding the amino acid sequence of SEQ ID NO:2. Both single-stranded and double-stranded RNA and DNA SVPH1–8 nucleic acid molecules are encompassed by the invention. These molecules can be used to detect both single-stranded and double-stranded RNA and DNA variants of SVPH1–8 encompassed by the invention. A double-stranded DNA probe allows the detection of nucleic acid molecules equivalent to either strand of the nucleic acid molecule. Isolated nucleic acid molecules that hybridize to a denatured, double-stranded DNA comprising the DNA sequence of SEQ ID NO:1 or an isolated nucleic acid molecule encoding the amino acid sequence of SEQ ID NO:2 under conditions of moderate stringency in 50% formamide and 6×SSC, at 42° C. with washing conditions of 60° C., 0.5×SSC, 0.1% SDS are encompassed by the invention.

The invention further encompasses isolated nucleic acid molecules derived by in vitro mutagenesis from SEQ ID NO:1. In vitro mutagenesis would include numerous techniques known in the art including, but not limited to, site-directed mutagenesis, random mutagenesis, and in vitro nucleic acid synthesis. The invention also encompasses isolated nucleic acid molecules degenerate from SEQ ID NO:1 as a result of the genetic code, isolated nucleic acid molecules that are allelic variants of human SVPH1–8 DNA, or a species homolog of SVPH1–8 DNA. The invention also encompasses recombinant vectors that direct the expression of these nucleic acid molecules and host cells transformed or transfected with these vectors.

The invention also encompasses isolated polypeptides encoded by these nucleic acid molecules, including isolated polypeptides having a molecular weight of approximately 81 kD as determined by SDS-PAGE and isolated polypeptides in non-glycosylated form. Isolated polyclonal or monoclonal antibodies that bind to these polypeptides are encompassed by the invention. The invention further encompasses methods for the production of SVPH1–8 polypeptides including culturing a host cell under conditions promoting expression and recovering the polypeptide from the culture medium. Especially, the expression of SVPH1–8 polypeptides in bacteria, yeast, plant, and animal cells is encompassed by the invention.

In addition, assays utilizing SVPH1–8 polypeptides to screen for potential inhibitors of activity associated with SVPH1–8 polypeptide counter-structure molecules, and methods of using SVPH1–8 polypeptides as therapeutic agents for the treatment of diseases mediated by SVPH1–8 polypeptide counter-structure molecules are encompassed by the invention. Further, methods of using SVPH1–8 polypeptides in the design of inhibitors thereof are also an aspect of the invention.

The invention further encompasses the fragmented peptides produced from SVPH1–8 polypeptides by chemical or enzymatic treatment. In addition, forms of SVPH1–8 polypeptide molecular weight markers and fragmented peptides thereof, wherein at least one of the sites necessary for fragmentation by chemical or enzymatic means has been mutated, are an aspect of the invention.

The invention also encompasses a method for the visualization of SVPH1–8 polypeptide molecular weight markers and fragmented peptides thereof using electrophoresis. The invention further includes a method for using SVPH1–8 polypeptide molecular weight markers and fragmented peptides thereof as molecular weight markers that allow the estimation of the molecular weight of a protein or a fragmented protein sample. The invention farther encompasses methods for using SVPH1–8 polypeptides and fragmented peptides thereof as markers, which aid in the determination of the isoelectric point of a sample protein. The invention also encompasses methods for using SVPH1–8 polypeptides and fragmented peptides thereof as controls for establishing the extent of fragmentation of a protein sample.

Further encompassed by this invention are kits to aid the determination of molecular weights of a sample protein utilizing SVPH1–8 polypeptide molecular weight markers, fragmented peptides thereof, and forms of SVPH1–8 polypeptide molecular weight markers, wherein at least one of the sites necessary for fragmentation by chemical or enzymatic means has been mutated.

Further encompassed by this invention are methods of using SVPH1–8 nucleic acids, polypeptides, and antibodies as cell and tissue markers in the identification and purification of SVPH1–8 expressing cells.

DETAILED DESCRIPTION OF THE INVENTION

A cDNA encoding human SVPH1–8 polypeptide has been isolated and is disclosed in SEQ ID NO:1.

```
                                              (SEQ ID NO:1)
ATGGCAGTGGATGGGACCCTCGTGTACATCAGGGTCACTCTTCTGCTGCT

CTGGCTTGGGGTATTTTTGTCTATTTCCGGCTACTGTCAGGCTGGGCCCT

CCCAGCATTTCACTTCCCCGGAAGTGGTGATCCCCTTGAAGGTGATCAGC

AGGGGCAGAAGTGCAAAGGCTCCTGGATGGCTCTCCTATAGTCTGCGGTT

TGGGGGCCAGAAACACGTTGTTCATATGAGGGTCAAGAAGCTCTTAGTTT

CTAGACACCTCCCAGTGTTCACCTACACAGATGAGCGTGCACTCCTGGAG

GATCAGCTCTTCATCCCAGATGACTGTTACTATCATGGTTACGTGGAGGG

TGCCCCTGAGTCTCTGGTTGTGTTCAGTGCTTGTTTTGGGGGCTTTCGAG

GAGTATTAAAAATAAGTGGCCTCACTTATGAAATTGAACCCATCAGGCAC

TCTGCCACATTTGAACACCTGGTTTACAAAGTAAACAGTAATGAGACACA

ATTCCCAGCTATGAGATGTGGCTTAACAGAGAAGGAAGTAGCACGCCAAC

AGTTGGAATTTGAAGAGGCTGAGAACTCAGCTCTGGAACCAAAATCTGCT

GGTGACTGGTGGACTCATGCATGGTTTCTGGAGCTAGTTGTTGTGGTGAA

CCATGATTTCTTCATTTACTCTCAAAGCAACATCTCAAAGGTGCAAGAGG

ATGTATTTCTTGTTGTCAACATAGTGGATTCCATGTATCAGCAGTTAGGT

ACTTACATAATTTTGATTGGAATTGAAATTTGGAATCAAGGAAATGTTTT
```

-continued

CCCAATGACAAGCATAGAACAGGTCCTGAACGATTTCTCTCAATGGAAAC

AAATCAGTCTTTCCCAGCTACAGCATGATGCTGCACATATGTTCATAAAA

AATTCACTTATAAGTATACTTGGCCTAGCCTATGTTGCAGGAATATGTCG

TCCACCTATTGATTGTGGAGTTGATAATTTTCAAGGAGATACCTGGTCTC

TTTTTGCCAACACTGTGGCCCATGAGTTAGGTCATACGTTGGGTATGCAG

CATGATGAAGAATTCTGTTTTTGTGGGGAAAGAGGTTGCATCATGAATAC

TTTTAGAGTGCCAGCAGAGAAATTCACCAATTGCAGTTACGCTGATTTTA

TGAAGACCACCTTAAACCAGGGATCATGTCTGCATAATCCTCCAAGATTG

GGGGAAATCTTTATGCTAAAGCGCTGTGGGAATGGTGTGGTTGAAAGAGA

AGAGCAGTGTGACTGTGGATCCGTACAGCAGTGTGAACAAGACGCCTGTT

GTCTGTTGAACTGCACTCTAAGGCCTGGGGCTGCCTGTGCTTTTGGGCTT

TGTTGCAAAGACTGCAAGTTCATGCCATCAGGGGAACTCTGTAGACAAGA

GGTCAATGAATGTGACCTTCCAGAATGGTGCAATGGAACATCTCATCAGT

GTCCAGAAGATAGATATGTGCAGGACGGGATCCCCTGTAGTGACAGTGCC

TACTGCTATCAAAAGAGGTGTAATAACCATGACCAGCATTGCAGGGAGAT

TTTTGGTAAAGATGCAAAAAGTGCATCTCAGAATTGCTATAAAGAAATCA

ACTCTCAGGGAAACCGTTTTGGTCACTGTGGTATAAATGGCACAACATAC

CTAAAATGTCATATCTCTGATGTCTTTTGTGGGAGAGTTCAATGTGAGAA

TGTGAGAGACATTCCTCTTCTCCAAGATCATTTTACTTTGCAGCACACTC

ATATCAATGGTGTCACCTGCTGGGGTATTGACTATCATTTAAGGATGAAC

ATATCTGACATTGGTGAAGTGAAAGATGGTACTGTGTGTGGCCCAGGAAA

GATCTGCATCCATAAGAAGTGTGTCAGTCTGTCTGTCTTGTCACATGTCT

GCCTTCCTGAGACCTGCAATATGAAGGGGATCTGCAATAACAAACATCAC

TGCCACTGTGGCTATGGGTGGTCCCCACCCTACTGCCAGCACAGAGGCTA

TGGGGGCAGTATTGACAGTGGCCCAGCATCTGCAAAGAGAGGAGTTTTTT

TGCCGCTGATTGTGATTCCTTCTTTGTCTGTTTTGACTTTCCTGTTTACT

GTCGGGCTTCTTATGTATCTACGACAATGTTCTGGTCCCAAAGAAACTAA

GGCTCATTCATCAGGTTAA

By Northern blot analysis using an SVPH1–8 nucleic acid probe, expression of SVPH1–8 RNA was detected only in testis. Therefore, SVPH1–8 expression can be used as a marker for testis cells and tissue.

This discovery of the cDNA encoding human SVPH1–8 polypeptide enables construction of expression vectors comprising nucleic acid sequences encoding SVPH1–8 polypeptides; host cells transfected or transformed with the expression vectors; biologically active human SVPH1–8 proteinase and SVPH1–8 molecular weight markers as isolated and purified proteins; and antibodies immunoreactive with SVPH1–8 polypeptides.

SVPH1–8 DNA (SEQ ID NO:1) encodes SVPH1–8 polypeptide (SEQ ID NO:2):

(SEQ ID NO:2)
MAVDGTLVYIRVTLLLLWLGVFLSISGYCQAGPSQHFTSPEVVIPLKVIS

RGRSAKAPGWLSYSLRFGGQKHVVHMRVKKLLVSRHLPVFTYTDERALLE

DQLFIPDDCYYHGYVEGAPESLVVFSACFGGFRGVLKISGLTYEIEPIRH

SATFEHLVYKVNSNETQFPAMRCGLTEKEVARQQLEFEEAENSALEPKSA

GDWWTHAWFLELVVVVNHDFFIYSQSNISKVQEDVFLVVNIVDSMYQQLG

TYIILIGIEIWNQGNVFPMTSIEQVLNDFSQWKQISLSQLQHDAAHMFIK

NSLISILGLAYVAGICRPPIDCGVDNFQGDTWSLFANTVAHELGHTLGMQ

HDEEFCFCGERGCIMNTFRVPAEKFTNCSYADFMKTTLNQGSCLHNPPRL

GEIFMLKRCGNGVVEREEQCDCGSVQQCEQDACCLLNCTLRPGAACAFGL

CCKDCKFMPSGELCRQEVNECDLPEWCNGTSHQCPEDRYVQDGIPCSDSA

YCYQKRCNNHDQHCREIFGKDAKSASQNCYKEINSQGNRFGHCGINGTTY

LKCHISDVFCGRVQCENVRDIPLLQDHFTLQHTHINGVTCWGIDYHLRMN

ISDIGEVKDGTVCGPGKICIHKKCVSLSVLSHVCLPETCNMKGICNNKHH

CHCGYGWSPPYCQHRGYGGSIDSGPASAKRGVFLPLIVIPSLSVLTFLFT

VGLLMYLRQCSGPKETKAHSSG.

SVPH1–8 polypeptide (SEQ ID NO:2) has all of the conserved domain structures found in mammalian adamalysins (ADAMS): signal sequence (amino acids 1–26 of SEQ ID NO:2), pro domain (amino acids 27–198 of SEQ ID NO:2), catalytic domain including the three conserved His residues (amino acids 199–397 of SEQ ID NO:2), disintegrin domain (amino acids 398–501 of SEQ ID NO:2), Cys-rich domain (amino acids 502–680 of SEQ ID NO:2), transmembrane domain (amino acids 681–707 of SEQ ID NO:2), and a cytoplasmic domain (amino acids 708–722 of SEQ ID NO:2).

ADAMS 1–6 have been implicated in fertilization and/or spermatogenesis (Barker, H. L., Perry, A. C., Jones, R., and Hall, L., *Biochim Biophys Acta,* 1218, 429–31, 1994; Blobel, C. P., Wolfsberg, T. G., Turck, C. W., Myles, D. G., Primakoff, P., and White, J. M. , *Nature,* 356, 248–252, 1992; Evans, J. P., Schultz, R. M., and Kopf, G. S., *J. Cell Sci,* 108, 3267–3278, 1995; Perry, A. C., Barker, H. L., Jones, R., and Hall., L., *Biochim Biophys Acta,* 1207, 134–137, 1994; Perry, A. C., Gichuhi, P. M., Jones, R., and Hall; L., *Biochem J.,* 307, 843–850, 1995; Perry, A. C., Jones, R., and Hall, L., Biochem J., 312, 239–244, 1995; Wolfsberg, T. G., Bazan, J. F., Blobel, C. P., Mules, D. G., Primakoff, P., and White, J. M., *Proc Natl Acad Sci USA,* 90, 10783–10787, 1993; and Wolfsberg, T. G., Straight, P. D., Gerena, R. L., Huovila, A. P., Primakoff, P., Myles, D. G., and White, J. M., *Dev Biol,* 169, 378–383, 1995). The finding that SVPH1–8 is specifically expressed in testis by Northern analysis also implicates this family member in fertilization and/or spermatogenesis. In addition, while ADAM1 has been found to be required for the fusion of sperm and egg, humans do not have an active form of this gene. Thus SVPH1–8 may be the human equivalent. The SVPH1–8 catalytic domain is required for biological activity. A proteinase inhibitor of the catalytic domain would inhibit SVPH1–8 activity and would be useful as a method for birth control. Also, an inhibitor of the disintegrin domain of SVPH1–8 may affect fertilization.

SVPH1–8 proteinase is a member of the snake venom protease family, and is homologous to the TACE protein. TACE is a proteinase required for the shedding of membrane proteins including TNFα, p80 TNFR, p60TNFR, L-selectin, type II IL-1R, and β-amyloid precursor protein. SVPH1–8 proteinase also shows homology with fertilin-α, which is required for binding of sperm to egg; meltrin-α, which is required for the fusion of myoblasts into muscle cells; reprolysin, which cleaves myelin basic protein; and kuzbanian, which is a *Drosophila* homologue of reprolysin, and is required for neurogenesis and axonal extension. The proteinase activity of SVPH1–8 is likely involved in the shedding of membrane proteins.

The protease activity may be involved in sperm/egg fusion. Thus, an inhibitor may be a contraceptive agent. The disintegrin domain of some homologues have been found to bind integrin. The disintegrin domain of fertilin-α and meltrin-α have been implicated in sperm/egg fusion and myoblast fusion, respectively. Using the disintegrin domain of SVPH1–8 in a screen, inhibitors of cell fusion could be found that are useful as contraceptive agents.

In one embodiment of this invention, the expression of recombinant SVPH1–8 polypeptides can be accomplished utilizing fusion of sequences encoding SVPH1–8 polypeptides to sequences encoding another polypeptide to aid in the purification of SVPH1–8 polypeptides. An example of such a fusion is a fusion of sequences encoding a SVPH1–8 polypeptide to sequences encoding the product of the malE gene of the pMAL-c2 vector of New England Biolabs, Inc. Such a fusion allows for affinity purification of the fusion protein, as well as separation of the maltose binding protein portion of the fusion protein from the SVPH1–8 polypeptide after purification. It is understood of course that many different vectors and techniques can be used for the expression and purification of SVPH1–8 polypeptides and that this embodiment in no way limits the scope of the invention.

The insertion of DNA encoding the SVPH1–8 polypeptide into the pMAL-c2 vector can be accomplished in a variety of ways using known molecular biology techniques. The preferred construction of the insertion contains a termination codon adjoining the carboxyl terminal codon of the SVPH1–8 polypeptide. In addition, the preferred construction of the insertion results in the fusion of the amino terminus of the SVPH1–8 polypeptide directly to the carboxyl terminus of the Factor Xa cleavage site in the pMAL-c2 vector. A DNA fragment can be generated by PCR using SVPH1–8 DNA as the template DNA and two oligonucleotide primers. Use of the oligonucleotide primers generates a blunt-ended fragment of DNA that can be isolated by conventional means. This PCR product can be ligated together with pMAL-p2 (digested with the restriction endonuclease Xmn I) using conventional means. Positive clones can be identified by conventional means. Induction of expression and purification of the fusion protein can be performed as per the manufacturer's instructions. This construction facilitates a precise separation of the SVPH1–8 polypeptide from the fused maltose binding protein utilizing a simple protease treatment as per the manufacturer's instructions. In this manner, purified SVPH1–8 polypeptide can be obtained. Furthermore, such a constructed vector can be easily modified using known molecular biology techniques to generate additional fusion proteins.

Another preferred embodiment of the invention is the use of SVPH1–8 polypeptides as molecular weight markers to estimate the apparent molecular weight of a sample protein by gel electrophoresis. An isolated and purified SVPH1–8 polypeptide molecular weight marker according to the invention has a molecular weight of approximately 80,766 Daltons in the absence of glycosylation. The SVPH1–8 polypeptide, together with a sample protein, can be resolved by denaturing polyacrylamide gel electrophoresis by conventional means (U. K. Laemmli, *Nature* 227:680–685, 1970) in two separate lanes of a gel containing sodium dodecyl sulfate and a concentration of acrylamide between 6–20%. Proteins on the gel can be visualized using a conventional staining procedure. The SVPH1–8 polypeptide molecular weight marker can be used as a molecular weight marker in the estimation of the apparent molecular weight of the sample protein. The unique amino acid sequence of SVPH1–8 (SEQ ID NO:2) specifies a molecular weight of approximately 80,766 Daltons. Therefore, the SVPH1–8 polypeptide molecular weight marker serves particularly well as a molecular weight marker for the estimation of the apparent molecular weight of sample proteins that have apparent molecular weights close to 80,766 Daltons. The use of this polypeptide molecular weight marker allows an increased accuracy in the determination of apparent molecular weight of proteins that have apparent molecular weights close to 80,766 Daltons. It is understood of course that many different techniques can be used for the determination of the molecular weight of a sample protein using SVPH1–8 polypeptides and that this embodiment in no way limits the scope of the invention.

Another preferred embodiment of the invention is the use of SVPH1–8 fragmented peptide molecular weight markers, generated by chemical fragmentation of SVPH1–8 polypeptide, as molecular weight markers to estimate the apparent molecular weight of a sample protein by gel electrophoresis. Isolated and purified SVPH1–8 polypeptide can be treated with cyanogen bromide under conventional conditions that result in fragmentation of the SVPH1–8 polypeptide molecular weight marker by specific hydrolysis on the carboxyl side of the methionine residues within the SVPH1–8 polypeptide (E. Gross, *Methods in Enz.* 11:238–255, 1967). Due to the unique amino acid sequence of the SVPH1–8 polypeptide, the fragmentation of SVPH1–8 polypeptide molecular weight markers with cyanogen bromide generates a unique set of SVPH1–8 fragmented peptide molecular weight markers. The distribution of methionine residues determines the number of amino acids in each peptide and the unique amino acid composition of each peptide determines its molecular weight.

The unique set of SVPH1–8 fragmented peptide molecular weight markers generated by treatment of SVPH1–8 polypeptide with cyanogen bromide comprises 14 fragmented peptides of at least 10 amino acids in size. The peptide encoded by amino acids 2–76 of SEQ ID NO:2 has a molecular weight of approximately 8,205 Daltons. The peptide encoded by amino acids 77–171 of SEQ ID NO:2 has a molecular weight of approximately 10,865 Daltons. The peptide encoded by amino acids 172–245 of SEQ ID NO:2 has a molecular weight of approximately 8,568 Daltons. The peptide encoded by amino acids 246–269 of SEQ ID NO:2 has a molecular weight of approximately 2,809 Daltons. The peptide encoded by amino acids 270–297 of SEQ ID NO:2 has a molecular weight of approximately 3,253 Daltons. The peptide encoded by amino acids 298–349 of SEQ ID NO:2 has a molecular weight of approximately 5,573 Daltons. The peptide encoded by amino acids 350–365 of SEQ ID NO:2 has a molecular weight of approximately 1,902 Daltons. The peptide encoded by amino acids 366–384 of SEQ ID NO:2 has a molecular weight of approximately 2,240 Daltons. The peptide encoded by amino acids 385–405 of SEQ ID NO:2 has a molecular weight of approximately 2,355 Daltons. The peptide encoded by amino acids 406–458 of SEQ ID NO:2 has a molecular weight of approximately 5,747 Daltons. The peptide encoded by amino acids 459–599 of SEQ ID NO:2 has a molecular weight of approximately 16,175 Daltons. The peptide encoded by amino acids 600–641 of SEQ ID NO:2 has a molecular weight of approximately 4,426 Daltons. The peptide encoded by amino acids 642–705 of SEQ ID NO:2 has a molecular weight of approximately 6,898 Daltons. The peptide encoded by amino acids 706–722 of SEQ ID NO:2 has a molecular weight of approximately 1,847 Daltons.

Therefore, cleavage of the SVPH1–8 polypeptide by chemical treatment with cyanogen bromide generates a unique set of SVPH1–8 fragmented peptide molecular weight markers. The unique and known amino acid sequence of these SVPH1–8 fragmented peptides allows the determination of the molecular weight of these fragmented peptide molecular weight markers. In this particular case, SVPH1–8 fragmented peptide molecular weight markers have molecular weights of approximately 8,205; 10,865; 8,568; 2,809; 3,253; 5,573; 1,902; 2,240; 2,355; 5,747; 16,175; 4,426; 6,898; and 1,847 Daltons.

The SVPH1–8 fragmented peptide molecular weight markers, together with a sample protein, can be resolved by denaturing polyacrylamide gel electrophoresis by conventional means in two separate lanes of a gel containing sodium dodecyl sulfate and a concentration of acrylamide between 10–20%. Proteins on the gel can be visualized using a conventional staining procedure. The SVPH1–8 fragmented peptide molecular weight markers can be used as molecular weight markers in the estimation of the apparent molecular weight of the sample protein. The unique amino acid sequence of SVPH1–8 specifies a molecular weight of approximately 8,205; 10,865; 8,568; 2,809; 3,253; 5,573; 1,902; 2,240; 2,355; 5,747; 16,175; 4,426; 6,898; and 1,847 Daltons for the SVPH1–8 fragmented peptide molecular weight markers. Therefore, the SVPH1–8 fragmented peptide molecular weight markers serve particularly well as molecular weight markers for the estimation of the apparent molecular weight of sample proteins that have apparent molecular weights close to 8,205; 10,865; 8,568; 2,809; 3,253; 5,573; 1,902; 2,240; 2,355; 5,747; 16,175; 4,426; 6,898; or 1,847 Daltons. Consequently, the use of these fragmented peptide molecular weight markers allows an increased accuracy in the determination of apparent molecular weight of proteins that have apparent molecular weights close to 8,205; 10,865; 8,568; 2,809; 3,253; 5,573; 1,902; 2,240; 2,355; 5,747; 16,175; 4,426; 6,898; or 1,847 Daltons.

In a further embodiment, the sample protein and the SVPH1–8 polypeptide can be simultaneously, but separately, treated with cyanogen bromide under conventional conditions that result in fragmentation of the sample protein and the SVPH1–8 polypeptide by specific hydrolysis on the carboxyl side of the methionine residues within the sample protein and the SVPH1–8 polypeptide. As described above, the SVPH1–8 fragmented peptide molecular weight markers generated by cleavage of the SVPH1–8 polypeptide with cyanogen bromide have molecular weights of approximately 8,205; 10,865; 8,568; 2,809; 3,253; 5,573; 1,902; 2,240; 2,355; 5,747; 16,175; 4,426; 6,898; and 1,847 Daltons.

The fragmented peptides from both the SVPH1–8 polypeptide and the sample protein can be resolved by denaturing polyacrylamide gel electrophoresis by conventional means in two separate lanes of a gel containing sodium dodecyl sulfate and a concentration of acrylamide between 10–20%. Fragmented peptides on the gel can be visualized using a conventional staining procedure. The SVPH1–8 fragmented peptide molecular weight markers can be used as molecular weight markers in the estimation of the apparent molecular weight of the fragmented proteins derived from the sample protein. As discussed above, the SVPH1–8 fragmented peptide molecular weight markers serve particularly well as molecular weight markers for the estimation of the apparent molecular weight of fragmented peptides that have apparent molecular weights close to 8,205; 10,865; 8,568; 2,809; 3,253; 5,573; 1,902; 2,240; 2,355; 5,747; 16,175; 4,426; 6,898; or 1,847 Daltons. Consequently, the use of these SVPH1–8 fragmented peptide molecular weight markers allows an increased accuracy in the determination of apparent molecular weight of fragmented peptides that have apparent molecular weights close to 8,205; 10,865; 8,568; 2,809; 3,253; 5,573; 1,902; 2,240; 2,355; 5,747; 16,175; 4,426; 6,898; or 1,847 Daltons. The extent of fragmentation of the SVPH1–8 polypeptide is further used as a control to determine the conditions expected for complete fragmentation of the sample protein. It is understood of course that many chemicals could be used to fragment SVPH1–8 polypeptides and that this embodiment in no way limits the scope of the invention.

In another embodiment, unique sets of SVPH1–8 fragmented peptide molecular weight markers can be generated from SVPH1–8 polypeptide using enzymes that cleave the polypeptide at specific amino acid residues. Due to the unique nature of the amino acid sequence of the SVPH1–8 polypeptide, cleavage at different amino acid residues will result in the generation of different sets of fragmented peptide molecular weight markers.

An isolated and purified SVPH1–8 polypeptide can be treated with Achromobacter protease I under conventional conditions that result in fragmentation of the SVPH1–8 polypeptide by specific hydrolysis on the carboxyl side of the lysine residues within the SVPH1–8 polypeptide (T. Masaki et al., Biochim. Biophys. Acta 660:44–50, 1981; T. Masaki et al., Biochim. Biophys. Acta 660:51–55, 1981). Due to the unique amino acid sequence of the SVPH1–8 polypeptide, the fragmentation of SVPH1–8 polypeptide molecular weight markers with Achromobacter protease I generates a unique set of SVPH1–8 fragmented peptide molecular weight markers. The distribution of lysine residues determines the number of amino acids in each peptide and the unique amino acid composition of each peptide determines its molecular weight.

The unique set of SVPH1–8 fragmented peptide molecular weight markers generated by treatment of SVPH1–8 polypeptide with Achromobacter protease I comprises 20 fragmented peptides of at least 10 amino acids in size. The generation of 20 fragmented peptides with this enzyme treatment of the SVPH1–8 polypeptide, as compared to the generation of 14 fragmented peptides with cyanogen bromide treatment of the SVPH1–8 polypeptide, clearly illustrate that the sizes of the fragmented peptide molecular weight markers will vary depending upon the fragmentation treatment utilized to fragment the SVPH1–8 polypeptide. Both the size and number of these fragments are dictated by the amino acid sequence of the SVPH1–8 polypeptide. Consequently, the number of fragmented peptides will also vary depending upon the fragmentation treatment utilized to fragment the SVPH1–8 polypeptide.

The peptide encoded by amino acids 1–47 of SEQ ID NO:2 has a molecular weight of approximately 5,130 Daltons. The peptide encoded by amino acids 57–71 of SEQ ID NO:2 has a molecular weight of approximately 1,665 Daltons. The peptide encoded by amino acids 81–137 of SEQ ID NO:2 has a molecular weight of approximately 6,451 Daltons. The peptide encoded by amino acids 138–160 of SEQ ID NO:2 has a molecular weight of approximately 2,702 Daltons. The peptide encoded by amino acids 161–178 of SEQ ID NO:2 has a molecular weight of approximately 2,023 Daltons. The peptide encoded by amino acids 179–198 of SEQ ID NO:2 has a molecular weight of approximately 2,316 Daltons. The peptide encoded by amino acids 199–230 of SEQ ID NO:2 has a molecular weight of approximately 3,794 Daltons. The peptide encoded by amino acids 231–283 of SEQ ID NO:2 has a molecular weight of approximately 6,173 Daltons. The peptide encoded by amino acids 284–300 of SEQ ID NO:2 has a molecular weight of approximately 1,966 Daltons. The peptide encoded by amino acids 301–374 of SEQ ID NO:2 has a molecular weight of approximately 8,112 Daltons. The peptide encoded by amino acids 375–385 of SEQ ID NO:2 has a molecular weight of approximately 1,325 Daltons. The peptide encoded by amino acids 386–407 of SEQ ID NO:2 has a molecular weight of approximately 2,468 Daltons. The peptide encoded by amino acids 408–453 of SEQ ID NO:2 has a molecular weight of approximately 4,882 Daltons. The peptide encoded by amino acids 457–505 of SEQ ID NO:2 has a molecular weight of approximately 5,629 Daltons. The peptide encoded by amino acids 506–520 of SEQ ID NO:2 has a molecular weight of approximately 1,855 Daltons. The peptide encoded by amino acids 532–552 of SEQ ID NO:2 has a molecular weight of approximately 2,308 Daltons. The peptide encoded by amino acids 553–608 of SEQ ID NO:2 has a molecular weight of approximately 6,474 Daltons. The peptide encoded by amino acids 624–642 of SEQ ID NO:2 has a molecular weight of approximately 2,061 Daltons. The peptide encoded by amino acids 649–679 of SEQ ID NO:2 has a molecular weight of approximately 3,314 Daltons. The peptide encoded by amino acids 680–714 of SEQ ID NO:2 has a molecular weight of approximately 3,877 Daltons.

Therefore, cleavage of the SVPH1–8 polypeptide by enzymatic treatment with Achromobacter protease I generates a unique set of SVPH1–8 fragmented peptide molecular weight markers. The unique and known amino acid sequence of these fragmented peptides allows the determination of the molecular weight of these SVPH1–8 fragmented peptide molecular weight markers. In this particular case, these SVPH1–8 fragmented peptide molecular weight markers have molecular weights of approximately 5,130; 1,665; 6,451; 2,702; 2,023; 2,316; 3,794; 6,173; 1,966; 8,112; 1,325; 2,468; 4,882; 5,629; 1,855; 2,308; 6,474; 2,061; 3,314; and 3,877 Daltons.

Once again, the SVPH1–8 fragmented peptide molecular weight markers, together with a sample protein, can be resolved by denaturing polyacrylamide gel electrophoresis by conventional means in two separate lanes of a gel containing sodium dodecyl sulfate and a concentration of acrylamide between 10–20%. Proteins on the gel can be visualized using a conventional staining procedure. The SVPH1–8 fragmented peptide molecular weight markers can be used as molecular weight markers in the estimation of the apparent molecular weight of the sample protein. The SVPH1–8 fragmented peptide molecular weight markers serve particularly well as molecular weight markers for the estimation of the apparent molecular weight of proteins that have apparent molecular weights close to 5,130; 1,665; 6,451; 2,702; 2,023; 2,316; 3,794; 6,173; 1,966; 8,112; 1,325; 2,468; 4,882; 5,629; 1, 855; 2,308; 6,474; 2,061; 3,314; or 3,877 Daltons. The use of these fragmented peptide molecular weight markers allows an increased accuracy in the determination of apparent molecular weight of proteins that have apparent molecular weights close to 5,130; 1,665; 6,451; 2,702; 2,023; 2,316; 3,794; 6,173; 1,966; 8,112; 1,325; 2,468; 4,882; 5,629; 1,855; 2,308; 6,474; 2,061; 3,314; or 3,877 Daltons.

In another embodiment, the sample protein and the SVPH1–8 polypeptide can be simultaneously, but separately, treated with Achromobacter protease I under conventional conditions that result in fragmentation of the sample protein and the SVPH1–8 polypeptide by specific hydrolysis on the carboxyl side of the lysine residues within the sample protein and the SVPH1–8 polypeptide. The SVPH1–8 fragmented peptide molecular weight markers and the fragmented peptides derived from the sample protein are resolved by denaturing polyacrylamide gel electrophoresis by conventional means in two separate lanes of a gel containing sodium dodecyl sulfate and a concentration of acrylamide between 10–20%. Fragmented peptides on the gel can be visualized using a conventional staining procedure. The SVPH1–8 fragmented peptide molecular weight markers can be used as molecular weight markers in the estimation of the apparent molecular weight of the sample protein. The SVPH1–8 fragmented peptide molecular weight markers serve particularly well as molecular weight markers for the estimation of the apparent molecular weight of fragmented peptides that have apparent molecular weights close to 5,130; 1,665; 6,451; 2,702; 2,023; 2,316; 3,794; 6,173; 1,966; 8,112; 1,325; 2,468; 4,882; 5,629; 1,855; 2,308; 6,474; 2,061; 3,314; or 3,877 Daltons. The use of these SVPH1–8 fragmented peptide molecular weight markers allows an increased accuracy in the determination of apparent molecular weight of fragmented peptides that have apparent molecular weights close to 5,130; 1,665; 6,451; 2,702; 2,023; 2,316; 3,794; 6,173; 1,966; 8,112; 1,325; 2,468; 4,882; 5,629; 1,855; 2,308; 6,474; 2,061; 3,314; or 3,877 Daltons. The extent of fragmentation of the SVPH1–8 polypeptide is further used as a control to determine the conditions expected for complete fragmentation of the sample protein. It is understood of course that many enzymes could be used to fragment SVPH1–8 polypeptides and that this embodiment in no way limits the scope of the invention.

In another embodiment, monoclonal and polyclonal antibodies against SVPH1–8 polypeptides can be generated. Balb/c mice can be injected intraperitoneally on two occasions at 3 week intervals with 10 μg of isolated and purified SVPH1–8 polypeptide or peptides based on the amino acid sequence of SVPH1–8 polypeptides in the presence of RIBI adjuvant (RIBI Corp., Hamilton, Mont.). Mouse sera are then assayed by conventional dot blot technique or antibody capture (ABC) to determine which animal is best to fuse. Three weeks later, mice are given an intravenous boost of 3 μg of the SVPH1–8 polypeptide or peptides, suspended in sterile PBS. Three days later, mice are sacrificed and spleen cells fused with Ag8.653 myeloma cells (ATCC) following established protocols. Briefly, Ag8.653 cells are washed several times in serum-free media and fused to mouse spleen cells at a ratio of three spleen cells to one myeloma cell. The fusing agent is 50% PEG: 10% DMSO (Sigma). Fusion is plated out into twenty 96-well flat bottom plates (Corning) containing HAT supplemented DMEM media and allowed to grow for eight days. Supernatants from resultant hybridomas are collected and added to a 96-well plate for 60 minutes that is first coated with goat anti-mouse Ig. Following washes, $^{125}$I-SVPH1–8 polypeptide or peptides are added to each well, incubated for 60 minutes at room temperature, and washed four times. Positive wells can be subsequently detected by autoradiography at −70° C. using Kodak X-Omat S film. Positive clones can be grown in bulk culture and supernatants are subsequently purified over a Protein A column (Pharmacia). It is understood of course that many techniques could be used to generate antibodies against SVPH1–8 polypeptides and fragmented peptides thereof and that this embodiment in no way limits the scope of the invention.

In another embodiment, antibodies generated against SVPH1–8 and fragmented peptides thereof can be used in combination with SVPH1–8 polypeptide or fragmented peptide molecular weight markers to enhance the accuracy in the use of these molecular weight markers to determine the apparent molecular weight and isoelectric point of a sample protein. SVPH1–8 polypeptide or fragmented peptide molecular weight markers can be mixed with a molar excess of a sample protein and the mixture can be resolved by two dimensional electrophoresis by conventional means. Polypeptides can be transferred to a suitable protein binding membrane, such as nitrocellulose, by conventional means.

Polypeptides on the membrane can be visualized using two different methods that allow a discrimination between the sample protein and the molecular weight markers. SVPH1–8 polypeptide or fragmented peptide molecular weight markers can be visualized using antibodies generated against these markers and conventional immunoblotting techniques. This detection is performed under conventional conditions that do not result in the detection of the sample protein. It is understood that it may not be possible to generate antibodies against all SVPH1–8 polypeptide fragments, since small peptides may not contain immunogenic epitopes. It is further understood that not all antibodies will work in this assay; however, those antibodies which are able to bind SVPH1–8 polypeptides and fragments can be readily determined using conventional techniques.

The sample protein is visualized using a conventional staining procedure. The molar excess of sample protein to SVPH1–8 polypeptide or fragmented peptide molecular weight markers is such that the conventional staining procedure predominantly detects the sample protein. The level of SVPH1–8 polypeptide or fragmented peptide molecular weight markers is such as to allow little or no detection of these markers by the conventional staining method. The preferred molar excess of sample protein to SVPH1–8 polypeptide molecular weight markers is between 2 and 100,000 fold. More preferably, the preferred molar excess of sample protein to SVPH1–8 polypeptide molecular weight markers is between 10 and 10,000 fold and especially between 100 and 1,000 fold.

The SVPH1–8 polypeptide or fragmented peptide molecular weight markers can be used as molecular weight and isoelectric point markers in the estimation of the apparent molecular weight and isoelectric point of the sample protein. The SVPH1–8 polypeptide or fragmented peptide molecular weight markers serve particularly well as molecular weight and isoelectric point markers for the estimation of apparent molecular weights and isoelectric points of sample proteins that have apparent molecular weights and isoelectric points close to that of the SVPH1–8 polypeptide or fragmented peptide molecular weight markers. The ability to simultaneously resolve the SVPH1–8 polypeptide or fragmented peptide molecular weight markers and the sample protein under identical conditions allows for increased accuracy in the determination of the apparent molecular weight and isoelectric point of the sample protein. This is of particular interest in techniques, such as two dimensional electrophoresis, where the nature of the procedure dictates that any markers should be resolved simultaneously with the sample protein.

In another embodiment, SVPH1–8 polypeptide or fragmented peptide molecular weight markers can be used as molecular weight and isoelectric point markers in the estimation of the apparent molecular weight and isoelectric point of fragmented peptides derived by treatment of a sample protein with a cleavage agent. It is understood of course that many techniques can be used for the determination of molecular weight and isoelectric point of a sample protein and fragmented peptides thereof using SVPH1–8 polypeptide molecular weight markers and peptide fragments thereof and that this embodiment in no way limits the scope of the invention.

SVPH1–8 polypeptide molecular weight markers encompassed by invention can have variable molecular weights, depending upon the host cell in which they are expressed. Glycosylation of SVPH1–8 polypeptide molecular weight markers and peptide fragments thereof in various cell types can result in variations of the molecular weight of these markers, depending upon the extent of modification. The size of SVPH1–8 polypeptide molecular weight markers can be most heterogeneous with fragments of SVPH1–8 polypeptide derived from the extracellular portion of the polypeptide. Consistent molecular weight markers can be obtained by using polypeptides derived entirely from the transmembrane and cytoplasmic regions, pretreating with N-glycanase to remove glycosylation, or expressing the polypeptides in bacterial hosts.

The interaction between SVPH1–8 and its counter-structure enables screening for small molecules that interfere with the SVPH1–8/SVPH1–8 counter-structure association and inhibit activity of SVPH1–8 or its counter-structure. For example, the yeast two-hybrid system developed at SUNY (described in U.S. Pat. No. 5,283,173 to Fields et al.) can be used to screen for inhibitors of SVPH1–8 as follows. SVPH1–8 and its counter-structure, or portions thereof responsible for their interaction, can be fused to the Gal4 DNA binding domain and Gal4 transcriptional activation domain, respectively, and introduced into a strain that depends on Gal4 activity for growth on plates lacking histidine. Compounds that prevent growth can be screened in order to identify SVPH1–8 inhibitors. Alternatively, the screen can be modified so that SVPH1–8/SVPH1–8 counter-structure interaction inhibits growth, so that inhibition of the interaction allows growth to occur. Another, in vitro, approach to screening for SVPH1–8 inhibition would be to immobilize one of the components (either SVPH1–8 or its counter-structure) in wells of a microtiter plate, and to couple an easily detected indicator to the other component. An inhibitor of the interaction is identified by the absence of the detectable indicator from the well.

In addition, SVPH1–8 polypeptides according to the invention are useful for the structure-based design of SVPH1–8 inhibitor. Such a design would comprise the steps of determining the three-dimensional structure of such the SVPH1–8 polypeptide, analyzing the three-dimensional structure for the likely binding sites of substrates, synthesizing a molecule that incorporates a predictive reactive site, and determining the inhibiting activity of the molecule.

Antibodies immunoreactive with SVPH1–8 polypeptides, and in particular, monoclonal antibodies against SVPH1–8 polypeptides, are now made available through the invention. Such antibodies can be useful for inhibiting SVPH1–8 polypeptide activity in vivo and for detecting the presence of SVPH1–8 polypeptides in a sample.

As used herein, the term "SVPH1–8 polypeptides" refers to a genus of polypeptides that further encompasses proteins having the amino acid sequence 1–722 of SEQ ID NO:2, as well as those proteins having a high degree of similarity (at least 90% identity) with such amino acid sequences and which proteins are biologically active. In addition, SVPH1–8 polypeptides refers to the gene products of the nucleotides 1–2169 of SEQ ID NO:1.

The isolated and purified SVPH1–8 polypeptide according to the invention has a molecular weight of approximately 80,766 Daltons in the absence of glycosylation. It is understood that the molecular weight of SVPH1–8 polypeptides can be varied by fusing additional peptide sequences to both the amino and carboxyl terminal ends of SVPH1–8 polypeptides. Fusions of additional peptide sequences at the amino and carboxyl terminal ends of SVPH1–8 polypeptides can be used to enhance expression of SVPH1–8 polypeptides or aid in the purification of the protein.

It is understood that fusions of additional peptide sequences at the amino and carboxyl terminal ends of SVPH1–8 polypeptides will alter some, but usually not all, of the fragmented peptides of SVPH1–8 polypeptides generated by enzymatic or chemical treatment.

It is understood that mutations can be introduced into SVPH1–8 polypeptides using routine and known techniques of molecular biology. It is further understood that a mutation can be designed so as to eliminate a site of proteolytic cleavage by a specific enzyme or a site of cleavage by a specific chemically induced fragmentation procedure. It is also understood that the elimination of the site will alter the peptide fingerprint of SVPH1–8 polypeptides upon fragmentation with the specific enzyme or chemical procedure.

The term "isolated and purified" as used herein, means that the SVPH1–8 polypeptide molecular weight markers or fragments thereof are essentially free of association with other proteins or polypeptides, for example, as a purification product of recombinant host cell culture or as a purified product from a non-recombinant source. The term "substantially purified" as used herein, refers to a mixture that contains SVPH1–8 polypeptide molecular weight markers or fragments thereof and is essentially free of association with other proteins or polypeptides, but for the presence of known proteins that can be removed using a specific antibody, and which substantially purified SVPH1–8 polypeptides or fragments thereof can be used as molecular weight markers. The term "purified" refers to either the "isolated and purified" form of SVPH1–8 polypeptides or the "substantially purified" form of SVPH1–8 polypeptides, as both are described herein.

A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

A SVPH1–8 polypeptide "variant" as referred to herein means a polypeptide substantially homologous to native SVPH1–8 polypeptides, but which has an amino acid sequence different from that of native SVPH1–8 polypeptides (human, murine or other mammalian species) because of one or more deletions, insertions or substitutions. The variant amino acid sequence preferably is at least 80% identical to a native SVPH1–8 polypeptide amino acid sequence, most preferably at least 90% identical. The percent identity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring SVPH1–8 variants are also encompassed by the invention. Examples of such variants are proteins that result from alternate mRNA splicing events or from proteolytic cleavage of the SVPH1–8 polypeptides. Variations attributable to proteolysis include, for example, differences in the N- or C-termini upon expression in different types of host cells, due to proteolytic removal of one or more terminal amino acids from the SVPH1–8 polypeptides (generally from 1–5 terminal amino acids).

As stated above, the invention provides isolated and purified, or homogeneous, SVPH1–8 polypeptides, both recombinant and non-recombinant. Variants and derivatives of native SVPH1–8 polypeptides that can be used as molecular weight markers can be obtained by mutations of nucleotide sequences coding for native SVPH1–8 polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques, January* 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

SVPH1–8 polypeptides can be modified to create SVPH1–8 polypeptide derivatives by forming covalent or aggregative conjugates with other chemical moieties, such as glycosyl groups, polyethylene glycol (PEG) groups, lipids, phosphate, acetyl groups and the like. Covalent derivatives of SVPH1–8 polypeptides can be prepared by linking the chemical moieties to functional groups on SVPH1–8 polypeptide amino acid side chains or at the N-terminus or C-terminus of a SVPH1–8 polypeptide or the extracellular domain thereof. Other derivatives of SVPH1–8 polypeptides within the scope of this invention include covalent or aggregative conjugates of SVPH1–8 polypeptides or peptide fragments with other proteins or polypeptides, such as by synthesis in recombinant culture as N-terminal or C-terminal fusions. For example, the conjugate can comprise a signal or leader polypeptide sequence (e.g. the α-factor leader of *Saccharomyces*) at the N-terminus of a SVPH1–8 polypeptide. The signal or leader peptide co-translationally or post-translationally directs transfer of the conjugate from its site of synthesis to a site inside or outside of the cell membrane or cell wall.

SVPH1–8 polypeptide conjugates can comprise peptides added to facilitate purification and identification of SVPH1–8 polypeptides. Such peptides include, for example, poly-His or the antigenic identification peptides described in U.S. Pat. No. 5,011,912 and in Hopp et al., *Bio/Technology* 6:1204, 1988.

The invention further includes SVPH1–8 polypeptides with or without associated native-pattern glycosylation. SVPH1–8 polypeptides expressed in yeast or mammalian expression systems (e.g., COS-1 or COS-7 cells) can be similar to or significantly different from a native SVPH1–8 polypeptide in molecular weight and glycosylation pattern, depending upon the choice of expression system. Expression of SVPH1–8 polypeptides in bacterial expression systems, such as *E. coli*, provides non-glycosylated molecules. Glycosyl groups can be removed through conventional methods, in particular those utilizing glycopeptidase. In general, glycosylated SVPH1–8 polypeptides can be incubated with a molar excess of glycopeptidase (Boehringer Mannheim).

Equivalent DNA constructs that encode various additions or substitutions of amino acid residues or sequences, or deletions of terminal or internal residues or sequences are encompassed by the invention. For example, N-glycosylation sites in the SVPH1–8 polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

The invention further encompasses isolated fragments and oligonucleotides derived from the nucleotide sequence of SEQ ID NO:1, including nucleotides 1–78, 79–594, 595–1191, 1192–1503, 1504–2040, 2041–2121, and 2122–2166. The invention also encompasses polypeptides encoded by these fragments and oligonucleotides.

Nucleic acid sequences within the scope of the invention include isolated DNA and RNA sequences that hybridize to the native SVPH1–8 nucleotide sequences disclosed herein under conditions of moderate or severe stringency, and which encode SVPH1–8 polypeptides. As used herein, conditions of moderate stringency, as known to those having ordinary skill in the art, and as defined by Sambrook et al. *Molecular Cloning: A Laboratory Manual,* 2 ed. Vol. 1, pp. 1.101–104, Cold Spring Harbor Laboratory Press, (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of about 60° C., 0.5×SSC, 0.1% SDS. Conditions of high stringency are defined as hybridization conditions as above, and with washing at 68° C., 0.2×SSC, 0.1% SDS. The skilled artisan will recognize that the temperature and wash solution salt concentration can be adjusted as necessary according to factors such as the length of the probe.

Due to the known degeneracy of the genetic code, wherein more than one codon can encode the same amino acid, a DNA sequence can vary from that shown in SEQ ID NO:1 and still encode a SVPH1–8 polypeptide having the amino acid sequence of SEQ ID NO:2. Such variant DNA sequences can result from silent mutations (e.g., occurring during PCR amplification), or can be the product of deliberate mutagenesis of a native sequence.

The invention thus provides equivalent isolated DNA sequences encoding SVPH1–8 polypeptides, selected from: (a) DNA derived from the coding region of a native mammalian SVPH1–8 gene; (b) cDNA comprising the nucleotide sequence 1–2169 of SEQ ID NO:1; (c) DNA capable of hybridization to a DNA of (a) under conditions of moderate stringency and which encodes SVPH1–8 polypeptides; and (d) DNA which is degenerate as a result of the genetic code to a DNA defined in (a), (b) or (c) and which encodes SVPH1–8 polypeptides. SVPH1–8 polypeptides encoded by such DNA equivalent sequences are encompassed by the invention.

DNA that is equivalent to the DNA sequence of SEQ ID NO:1 will hybridize under moderately stringent conditions to the double-stranded native DNA sequence that encode polypeptides comprising amino acid sequences of 1–722 of SEQ ID NO:2. Examples of SVPH1–8 polypeptides encoded by such DNA, include, but are not limited to, SVPH1–8 polypeptide fragments and SVPH1–8 polypeptides comprising inactivated N-glycosylation site(s), inactivated protease processing site(s), or conservative amino acid substitution(s), as described above. SVPH1–8 polypeptides encoded by DNA derived from other mammalian species, wherein the DNA will hybridize to the complement of the DNA of SEQ ID NO:1 are also encompassed.

SVPH1–8 polypeptide-binding proteins, such as the anti-SVPH1–8 polypeptide antibodies of the invention, can be bound to a solid phase such as a column chromatography matrix or a similar substrate suitable for identifying, separating or purifying cells that express SVPH1–8 polypeptides on their surface. For example, the expression of SVPH1–8 in testis indicates that anti-SVPH1–8 polypeptide antibodies could be used to identify, separate, or purify testicular cells using conventional techniques. Adherence of SVPH1–8 polypeptide-binding proteins to a solid phase contacting surface can be accomplished by any means, for example, magnetic microspheres can be coated with SVPH1–8 polypeptide-binding proteins and held in the incubation vessel through a magnetic field. Suspensions of cell mixtures are contacted with the solid phase that has SVPH1–8 polypeptide-binding proteins thereon. Cells having SVPH1–8 polypeptides on their surface bind to the fixed SVPH1–8 polypeptide-binding protein and unbound cells then are washed away. This affinity-binding method is useful for purifying, screening or separating such SVPH1–8 polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing SVPH1–8 polypeptide-expressing cells first can be incubated with a biotinylated SVPH1–8 polypeptide-binding protein. Incubation periods are typically at least one hour in duration to ensure sufficient binding to SVPH1–8 polypeptides. The resulting mixture then is passed through a column packed with avidin-coated beads, whereby the high affinity of biotin for avidin provides the binding of the SVPH1–8 polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable SVPH1–8 polypeptide-binding proteins are anti-SVPH1–8 polypeptide antibodies, and other proteins that are capable of high-affinity binding of SVPH1–8 polypeptides. A preferred SVPH1–8 polypeptide-binding protein is an anti-SVPH1–8 polypeptide monoclonal antibody.

SVPH1–8 polypeptides can exist as oligomers, such as covalently linked or non-covalently linked dimers or trimers. Oligomers can be linked by disulfide bonds formed between cysteine residues on different SVPH1–8 polypeptides. In one embodiment of the invention, a SVPH1–8 polypeptide dimer is created by fusing SVPH1–8 polypeptides to the Fc region of an antibody (e.g., IgGl) in a manner that does not interfere with biological activity of SVPH1–8 polypeptides. The Fc polypeptide preferably is fused to the C-terminus of a soluble SVPH1–8 polypeptide (comprising only the extracellular domain). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the SVPH1–8 polypeptide:Fc fusion protein is inserted into an appropriate expression vector. SVPH1–8 polypeptide:Fc fusion proteins are allowed to assemble much like antibody molecules, whereupon interchain disulfide bonds form between Fc polypeptides, yielding divalent SVPH1–8 polypeptides. If fusion proteins are made with both heavy and light chains of an antibody, it is possible to form a SVPH1–8 polypeptide oligomer with as many as four SVPH1–8 polypeptides extracellular regions. Alternatively, one can link two soluble SVPH1–8 polypeptide domains with a peptide linker.

Recombinant expression vectors containing a nucleic acid sequence encoding SVPH1–8 polypeptides can be prepared using well known methods. The expression vectors include a SVPH1–8 DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the SVPH1–8 DNA sequence. Thus, a promoter nucleotide sequence is operably linked to a SVPH1–8 DNA sequence if the promoter nucleotide sequence controls the transcription of the SVPH1–8 DNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with SVPH1–8 polypeptides can be incorporated into expression vectors. For example, a DNA sequence for a signal peptide (secretory leader) can be fused in-frame to the SVPH1–8 nucleotide sequence so that the SVPH1–8 polypeptide is initially translated as a fusion protein comprising the signal peptide. A signal peptide that is functional in the intended host cells enhances extracellular secretion of the SVPH1–8 polypeptide. The signal peptide can be cleaved from the SVPH1–8 polypeptide upon secretion of SVPH1–8 polypeptide from the cell.

Suitable host cells for expression of SVPH1–8 polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce SVPH1–8 polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a SVPH1–8 polypeptide can include an N-terminal methionine residue to facilitate expression of the recombinant polypeptide in the prokaryotic host cell. The N-terminal Met can be cleaved from the expressed recombinant SVPH1–8 polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct en expression vector using pBR322, an appropriate promoter and a SVPH1–8 DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776), and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection, which incorporate derivatives of the λ $P_L$ promoter, include plasmid pHUB2 (resident in *E. coli* strain JMB9 (ATCC 37092)) and pPLc28 (resident in *E. coli* RR1 (ATCC 53082)).

SVPH1–8 DNA may be cloned in-frame into the multiple cloning site of an ordinary bacterial expression vector. Ideally the vector would contain an inducible promoter upstream of the cloning site, such that addition of an inducer leads to high-level production of the recombinant protein at a time of the investigator's choosing. For some proteins, expression levels may be boosted by incorporation of codons encoding a fusion partner (such as hexahistidine) between the promoter and the gene of interest. The resulting "expression plasmid" may be propagated in a variety of strains of *E. coli*.

For expression of the recombinant protein, the bacterial cells are propagated in growth medium until reaching a pre-determined optical density. Expression of the recombinant protein is then induced, e.g. by addition of IPTG (isopropyl-b-D-thiogalactopyranoside), which activates expression of proteins from plasmids containing a lac operator/promoter. After induction (typically for 1–4 hours), the cells are harvested by pelleting in a centrifuge, e.g. at 5,000×G for 20 minutes at 4° C.

For recovery of the expressed protein, the pelleted cells may be resuspended in ten volumes of 50 mM Tris-HCI (pH 8)/1 M NaCl and then passed two or three times through a French press. Most highly-expressed recombinant proteins form insoluble aggregates known as inclusion bodies. Inclusion bodies can be purified away from the soluble proteins by pelleting in a centrifuge at 5,000×G for 20 minutes, 4° C. The inclusion body pellet is washed with 50 mM Tris-HCI (pH 8)/1% Triton X-100 and then dissolved in 50 mM Tris-HCI (pH 8)/8 M urea/0.1 M DTT. Any material that cannot be dissolved is removed by centrifugation (10,000×G for 20 minutes, 20° C.). The protein of interest will, in most cases, be the most abundant protein in the resulting clarified supernatant. This protein may be "refolded" into the active conformation by dialysis against 50 mM Tris-HCI (pH 8)/5 mM $CaCl_2$/5 mM $Zn(OAc)_2$/1 mM GSSG/0.1 mM GSH.

After refolding, purification can be carried out by a variety of chromatographic methods such as ion exchange or gel filtration. In some protocols, initial purification may be carried out before refolding. As an example, hexahistidine-tagged fusion proteins may be partially purified on immobilized Nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

SVPH1–8 polypeptides alternatively can be expressed in yeast host cells, preferably from the *Saccharomyces* genus (e.g., *S. cerevisiae*). Other genera of yeast, such as *Pichia, K. lactis*, or *Kluyveromyces*, can also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J Biol. Chem.* 255:2073, 1980), or other glycolytic enzymes (Hess et al., *J Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triose-phosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology*, 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* can be constructed by inserting DNA sequences from pBR322 for selection and replication in *E. coli* ($Amp^r$ gene and origin of replication) into the above-described yeast vectors.

The yeast α-factor leader sequence can be employed to direct secretion of a SVPH1–8 polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence can be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μg/ml adenine, and 20 μg/ml uracil.

Yeast host cells transformed by vectors containing ADH2 promoter sequence can be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian or insect host cell culture systems could also be employed to express recombinant SVPH1–8 polypeptides. Baculovirus systems for production of heterologous proteins in insect cells are reviewed by Luckow and Summers, *Bio/Technology* 6:47 (1988). Established cell lines of mammalian origin also can be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line (ATCC CRL 10478) derived from the African green monkey kidney cell line CVI (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15–69). Additional protocols using commercially available reagents, such as Lipofectamine (Gibco/BRL) or Lipofectamine-Plus, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. *Molecular Cloning: A Laboratory Manual*, 2 ed. Vol. 1–3, Cold Spring Harbor Laboratory Press, 1989). Selection of stable transformants can be performed using resistance to cytotoxic drugs as a selection method. Kaufman et al., *Meth. in Enzymology* 185:487–511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529–534) and the tripartite leader (TPL) and VA gene RNAs from Adenovirus 2 (Gingeras et al., *J Biol. Chem.* 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology*, 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in U.S. patent application Ser. No. 07/701,415, filed May 16, 1991, incorporated by reference herein. The vectors can be derived from retroviruses. In place of the native signal sequence, a heterologous signal sequence can be added, such as the signal sequence for LL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

An isolated and purified SVPH1–8 polypeptide molecular weight marker according to the invention can be produced by recombinant expression systems as described above or purified from naturally occurring cells. SVPH1–8 polypeptides can be substantially purified, as indicated by a single protein band upon analysis by SDS-polyacrylamide gel electrophoresis (SDS-PAGE).

One process for producing SVPH1–8 polypeptides comprises culturing a host cell transformed with an expression vector comprising a DNA sequence that encodes a SVPH1–8 polypeptide under conditions sufficient to promote expression of the SVPH1–8 polypeptide. SVPH1–8 polypeptide is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify SVPH1–8 polypeptides. Some or all of the foregoing purification steps, in various combinations, are well known and can be employed to provide an isolated and purified recombinant protein.

It is possible to utilize an affinity column comprising a SVPH1–8 polypeptide-binding protein, such as a monoclonal antibody generated against SVPH1–8 polypeptides, to affinity-purify expressed SVPH1–8 polypeptides. SVPH1–8 polypeptides can be removed from an affinity column using conventional techniques, e.g., in a high salt elution buffer and then dialyzed into a lower salt buffer for use or by changing pH or other components depending on the affinity matrix utilized.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express SVPH1–8 polypeptides as a secreted polypeptide in order to simplify purification. Secreted recombinant polypeptide from a yeast host cell fermentation can be purified by methods analogous to those disclosed by Urdal et al. (*J Chromatog.* 296:171, 1984). Urdal et al. describe two sequential, reversed-phase HPLC steps for purification of recombinant human IL-2 on a preparative HPLC column.

SVPH1–8 polypeptide molecular weight markers can be analyzed by methods including sedimentation, gel electrophoresis, chromatography, and mass spectrometry. SVPH1–8 polypeptides can serve as molecular weight markers using such analysis techniques to assist in the determination of the molecular weight of a sample protein. A molecular weight determination of the sample protein assists in the identification of the sample protein.

SVPH1–8 polypeptides can be subjected to fragmentation into peptides by chemical and enzymatic means. Chemical fragmentation includes the use of cyanogen bromide to cleave under neutral or acidic conditions such that specific cleavage occurs at methionine residues (E. Gross, *Methods in Enz.* 11:238–255, 1967). This can further include further steps, such as a carboxy-methylation step to convert cysteine residues to an unreactive species. Enzymatic fragmentation includes the use of a protease such as Asparaginylendopeptidase, Arginylendopeptidase, Achrombobacter protease 1, Trypsin, *Staphlococcus aureus* V8 protease, Endoproteinase Asp-N, or Endoproteinase Lys-C under conventional conditions to result in cleavage at specific amino acid residues. Asparaginylendopeptidase can cleave specifically on the carboxyl side of the asparagine residues present within SVPH1–8 polypeptides. Arginylendopeptidase can cleave specifically on the carboxyl side of the arginine residues present within SVPH1–8 polypeptides. Achrombobacter protease I can cleave specifically on the carboxyl side of the lysine residues present within SVPH1–8 polypeptides (Sakiyama and Nakat, U.S. Pat. No. 5,248,599; T. Masaki et al., *Biochim. Biophys. Acta* 660:44–50, 1981; T. Masaki et al., *Biochim. Biophys. Acta* 660:51–55, 1981). Trypsin can cleave specifically on the carboxyl side of the arginine and lysine residues present within SVPH1–8 polypeptides. *Staphlococcus aureus* V8 protease can cleave specifically on the carboxyl side of the aspartic and glutamic acid residues present within SVPH1–8 polypeptides (D. W. Cleveland, *J. Biol. Chem.* 3:1102–1106, 1977). Endoproteinase Asp-N can cleave specifically on the amino side of the asparagine residues present within SVPH1–8 polypeptides. Endoproteinase Lys-C can cleave specifically on the carboxyl side of the lysine residues present within SVPH1–8 polypeptides. Other enzymatic and chemical treatments can likewise be used to specifically fragment SVPH1–8 polypeptides into a unique set of specific peptide molecular weight markers.

The resultant fragmented peptides can be analyzed by methods including sedimentation, electrophoresis, chromatograpy, and mass spectrometry. The fragmented peptides derived from SVPH1–8 polypeptides can serve as molecular weight markers using such analysis techniques to assist in the determination of the molecular weight of a sample protein. Such a molecular weight determination assists in the identification of the sample protein. SVPH1–8 fragmented peptide molecular weight markers are preferably between 10 and 721 amino acids in size. More preferably, SVPH1–8 fragmented peptide molecular weight markers are between 10 and 100 amino acids in size. Even more preferable are SVPH1–8 fragmented peptide molecular weight markers between 10 and 50 amino acids in size and especially between 10 and 35 amino acids in size. Most preferable are SVPH1–8 fragmented peptide molecular weight markers between 10 and 20 amino acids in size.

Furthermore, analysis of the progressive fragmentation of SVPH1–8 polypeptides into specific peptides (D. W. Cleveland et al., *J. Biol. Chem.* 252:1102–1106, 1977), such as by altering the time or temperature of the fragmentation reaction, can be used as a control for the extent of cleavage of a sample protein. For example, cleavage of the same amount of SVPH1–8 polypeptide and sample protein under identical conditions can allow for a direct comparison of the extent of fragmentation. Conditions that result in the complete fragmentation of SVPH1–8 polypeptide can also result in complete fragmentation of the sample protein.

In addition, SVPH1–8 polypeptides and fragmented peptides thereof possess unique charge characteristics and, therefore, can serve as specific markers to assist in the determination of the isoelectric point of a sample protein or fragmented peptide using techniques such as isoelectric focusing. The technique of isoelectric focusing can be further combined with other techniques such as gel electrophoresis to simultaneously separate a protein on the basis of molecular weight and charge. An example of such a combination is that of two-dimensional electrophoresis (T. D. Brock and M. T. Madigan, *Biology of Microorganisms* 76–77 (Prentice Hall, 6d ed. 1991)). SVPH1–8 polypeptides and fragmented peptides thereof can be used in such analyses as markers to assist in the determination of both the isoelectric point and molecular weight of a sample protein or fragmented peptide.

Kits to aid in the determination of apparent molecular weight and isoelectric point of a sample protein can be assembled from SVPH1–8 polypeptides and peptide fragments thereof. Kits also serve to assess the degree of fragmentation of a sample protein. The constituents of such kits can be varied, but typically contain SVPH1–8 polypeptide and fragmented peptide molecular weight markers. Also, such kits can contain SVPH1–8 polypeptides wherein a site necessary for fragmentation has been removed. Furthermore, the kits can contain reagents for the specific cleavage of SVPH1–8 and the sample protein by chemical or enzymatic cleavage. Kits can further contain antibodies directed against SVPH1–8 polypeptides or fragments thereof.

Antisense or sense oligonucleotides comprising a single-stranded nucleic acid sequence (either RNA or DNA) capable of binding to a target SVPH1–8 mRNA sequence (forming a duplex) or to the SVPH1–8 sequence in the double-stranded DNA helix (forming a triple helix) can be made according to the invention. Antisense or sense oligonucleotides, according to the present invention, comprise a fragment of the coding region of SVPH1–8 cDNA (SEQ ID NO:1). Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of complexes that block translation (RNA) or transcription (DNA) by one of several means, including enhanced degradation of the duplexes, premature termination of transcription or translation, or by other means. The antisense oligonucleotides thus can be used to block expression of SVPH1–8 polypeptides. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation), but retain sequence specificity to be able to bind to target nucleotide sequences. Other examples of sense or antisense oligonucleotides include those oligonucleotides that are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes can be attached to sense or antisense oligonucleotides to modify binding specificities of the antisense or sense oligonucleotide for the target nucleotide sequence.

Antisense or sense oligonucleotides can be introduced into a cell containing the target nucleic acid sequence by any gene transfer method, including, for example, CaPO$_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also can be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide can be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Isolated and purified SVPH1–8 polypeptides or a fragment thereof can also be useful itself as a therapeutic agent in inhibiting IL-1 and TNF signaling. SVPH1–8 polypeptides are introduced into the intracellular environment by well-known means, such as by encasing the protein in liposomes or coupling it to a monoclonal antibody targeted to a specific cell type.

SVPH1–8 DNA, SVPH1–8 polypeptides, and antibodies against SVPH1–8 polypeptides can be used as reagents in a variety of research protocols. A sample of such research protocols are given in Sambrook et al. *Molecular Cloning: A Laboratory Manual,* 2 ed. Vol. 1–3, Cold Spring Harbor Laboratory Press, (1989).

For example, these reagents can serve as markers for cell specific or tissue specific expression of RNA or proteins. The expression of SVPH1–8 RNA only in testis indicates that the expression of SVPH1–8 RNA and polypeptides in testis derived cell lines or testicular tissues can be directly detected with the reagents of the invention. Therefore, these reagents can be used as markers for cell specific or tissue specific expression. Such markers can be used in the detection and purification of specific cell types, and in the analysis of various diseases associated with testis (Schmoll et al., *Semin Oncol* 25:174–185, 1998. Wahren et al., *J. Natl. Cancer Inst* 58:489–98; 1977; Beckstead, J. H., *Am J. Surg Pathol* 7:341–9, 1983; Burke et al., *Mod Pathol* 1:475–479, 1988; Rajpert-De Meyts et al., *Int J. Androl* 17:85–92, 1994; Mead et al., *J. Clin Oncol* 10:85–94, 1992). In one embodiment, the identification of testicular cells in testicular biopsies by the reagents of the invention can facilitate the detection and prognosis of testicular cancers. For example, testis cells can be detected using probes of SVPH1–8 nucleic acid using conventional techniques, including Northern blots and in situ RNA hybridization (reviewed in Jin et al., *J. Clin Lab Anal* 11:2–9, 1997; McNicol et al, *J. Pathol* 182: 250–261, 1997; Luke et al., *Cell Vis* 5:49–53, 1998). It is understood of course that many different techniques can be used for the identification and purification of SVPH1–8 expressing cells and that this embodiment in no way limits the scope of the invention.

Similarly, these reagents can be used to investigate constitutive and transient expression of SVPH1–8 RNA or polypeptides. SVPH1–8 DNA can be used to determine the chromosomal location of SVPH1–8 DNA and to map genes in relation to this chromosomal location. SVPH1–8 DNA can also be used to examine genetic heterogeneity and heredity through the use of techniques such as genetic fingerprinting, as well as to identify risks associated with genetic disorders. SVPH1–8 DNA can be further used to identify additional genes related to SVPH1–8 DNA and to establish evolutionary trees based on the comparison of sequences. SVPH1–8 DNA and polypeptides can be used to select for those genes or proteins that are homologous to SVPH1–8 DNA or polypeptides, through positive screening procedures such as Southern blotting and immunoblotting and through negative screening procedures such as subtraction.

SVPH1–8 proteinase can be used as a reagent in analyses with other proteinases to compare the substrate specificity and activity of the proteinases. Chimeric proteinases can be generated by swapping fragments of SVPH1–8 proteinase with other proteinases. Such chimeric proteinases can be analyzed with respect to altered activity and specificity.

The proteinase activity of SVPH1–8 can be used as a detergent additive for the removal of stains having a protein component, similar to the use of proteases described in U.S. Pat. No. 5,599,400 and U.S. Pat. No. 5,650,315. The detergent composition can contain other known detergent constituents, such as surfactants, foam enhancers, fillers, enzyme stabilizers, chlorine bleach scavengers, other proteolytic enzymes, bacteriocides, dyes, perfumes, diluents, solvents, and other conventional ingredients. The detergent composition preferably contains between 0.001% to 10% SVPH1–8 proteinase. SVPH1–8 proteinase can be included in a detergent composition or can be combined with other constituents at the time of use as an additive. The detergent additive can be formulated as a liquid, powder, granulate, slurry, or other conventional form of a detergent additive.

SVPH1–8 polypeptides can also be used as a reagent to identify (a) any protein that SVPH1–8 polypeptide regulates, and (b) other proteins with which it might interact. SVPH1–8 polypeptides could be used by coupling recombinant protein to an affinity matrix, or by using them as a bait in the 2-hybrid system.

When used as a therapeutic agent, SVPH1–8 polypeptides can be formulated into pharmaceutical compositions according to known methods. SVPH1–8 polypeptides can be combined in admixture, either as the sole active material or with other known active materials, with pharmaceutically suitable diluents (e.g., Tris-HCI, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain SVPH1–8 polypeptides complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of SVPH1–8 polypeptides.

Within an aspect of the invention, SVPH1–8 polypeptides, and peptides based on the amino acid sequence of SVPH1–8, can be utilized to prepare antibodies that specifically bind to SVPH1–8 polypeptides. The term "antibodies" is meant to include polyclonal antibodies, monoclonal antibodies, fragments thereof such as F(ab')2, and Fab fragments, as well as any recombinantly produced binding partners. Antibodies are defined to be specifically binding if they bind SVPH1–8 polypeptides with a $K_a$ of greater than or equal to about $10^7 M^{-1}$. Affinities of binding partners or antibodies can be readily determined using conventional techniques, for example those described by Scatchard et al., *Ann. N.Y Acad. Sci.*, 51:660 (1949).

Polyclonal antibodies can be readily generated from a variety of sources, for example, horses, cows, goats, sheep, dogs, chickens, rabbits, mice, or rats, using procedures that are well-known in the art. In general, purified SVPH1–8 polypeptides, or a peptide based on the amino acid sequence of SVPH1–8 polypeptides that is appropriately conjugated, is administered to the host animal typically through parenteral injection. The immunogenicity of SVPH1–8 polypeptides can be enhanced through the use of an adjuvant, for example, Freund's complete or incomplete adjuvant. Following booster immunizations, small samples of serum are collected and tested for reactivity to SVPH1–8 polypeptides. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radio-immunoassay, radio-immunoprecipitation, enzyme-linked immuno-sorbent assays (ELISA), dot blot assays, and sandwich assays, see U.S. Pat. Nos. 4,376,110 and 4,486,530.

Monoclonal antibodies can be readily prepared using well-known procedures, see for example, the procedures described in U.S. Pat. Nos. RE 32,011, 4,902,614, 4,543, 439, and 4,411,993; Monoclonal Antibodies, Hybridomas: *A New Dimension in Biological Analyses*, Plenum Press, Kennett, McKearn, and Bechtol (eds.), 1980. Briefly, the host animals, such as mice are injected intraperitoneally at least once, and preferably at least twice at about 3 week intervals with isolated and purified SVPH1–8 polypeptides or conjugated SVPH1–8 polypeptides, optionally in the presence of adjuvant. Mouse sera are then assayed by conventional dot blot technique or antibody capture (ABC) to determine which animal is best to fuse. Approximately two to three weeks later, the mice are given an intravenous boost of SVPH1–8 polypeptides or conjugated SVPH1–8 polypeptides. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow, for approximately eight days. Supernatants from resultant hybridomas are collected and added to a plate that is first coated with goat anti-mouse Ig. Following washes, a label, such as, $^{125}$I-SVPH1–8 polypeptides is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1–9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Other types of "antibodies" can be produced using the information provided herein in conjunction with the state of knowledge in the art. For example, antibodies that have been engineered to contain elements of human antibodies that are capable of specifically binding SVPH1–8 polypeptides are also encompassed by the invention.

Once isolated and purified, the antibodies against SVPH1–8 polypeptides can be used to detect the presence of SVPH1–8 polypeptides in a sample using established assay protocols. For example, antibodies against SVPH1–8 polypeptides can be used to detect or purify SVPH1–8 expressing cells, such as testis cells, by conventional techniques. Further, the antibodies of the invention can be used therapeutically to bind to SVPH1–8 polypeptides and inhibit its activity in vivo.

The purified SVPH1–8 polypeptides according to the invention will facilitate the discovery of inhibitors of SVPH1–8 polypeptides. The use of a purified SVPH1–8 polypeptide in the screening of potential inhibitors thereof is important and can eliminate or reduce the possibility of interfering reactions with contaminants.

In addition, SVPH1–8 polypeptides can be used for structure-based design of SVPH1–8 polypeptide-inhibitors. Such structure-based design is also known as "rational drug design." The SVPH1–8 polypeptides can be three-dimensionally analyzed by, for example, X-ray crystallography, nuclear magnetic resonance or homology modeling, all of which are well-known methods. The use of SVPH1–8 polypeptide structural information in molecular modeling software systems to assist in inhibitor design and inhibitor-SVPH1–8 polypeptide interaction is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of SVPH1–8 polypeptides for likely binding sites of substrates, synthesizing a new molecule that incorporates a predictive reactive site, and assaying the new molecule as described above.

The specification is most thoroughly understood in light of the teachings of the references cited within the specification, which are hereby incorporated by reference. The embodiments within the specification provide an illustration of embodiments of the invention and should not be construed to limit the scope of the invention. The skilled artisan recognizes many other embodiments are encompassed by the claimed invention.

What is claimed is:

1. An isolated nucleic acid molecule comprising a nucleotide sequence selected from the group consisting of:
   (a) SEQ ID NO:1;
   (b) a nucleotide sequence encoding SEQ ID NO:2;
   (c) nucleotides 595 through 1191 of SEQ ID NO:1 wherein said nucleic acid molecule encodes a polypeptide having proteinase activity;
   (d) a nucleotide sequence encoding amino acids 199 through 397 of SEQ ID NO:2, wherein said nucleic acid molecule encodes a polypeptide having proteinase activity; and
   (e) the nucleotide sequence of a nucleic acid molecule that hybridizes under high stringency in 6×SSC and 50% formamide at 42° C. with washing conditions of 0.2× SSC and 0.1% SDS at 68° C. to a nucleic acid consisting of SEQ ID NO:1 or its complement, wherein said nucleotide sequence encodes an SVPH1–8 variant having proteinase activity.

2. The isolated nucleic acid molecule of claim 1, wherein the nucleic acid molecule encodes a polypeptide having a molecular weight of approximately 81 kD as determined by SDS-PAGE.

3. The isolated nucleic acid molecule of claim 1, wherein the nucleic acid molecule encodes a polypeptide having proteinase activity and comprising an amino acid sequence selected from the group consisting of:
   (a) amino acids 27 through 397 of SEQ ID NO:2;
   (b) amino acids 27 through 501 of SEQ ID NO:2;
   (c) amino acids 27 through 680 of SEQ ID NO:2;
   (d) amino acids 199 through 397 of SEQ ID NO:2;
   (e) amino acids 199 through 501 of SEQ ID NO:2; and
   (f) amino acids 199 through 680 of SEQ ID NO:2.

4. An isolated nucleic acid molecule encoding a fusion protein and comprising the nucleotide sequence of the nucleic acid molecule of claim 1, wherein said nucleic acid molecule encoding a fusion protein further comprises a nucleotide sequence encoding a polypeptide selected from the group consisting of an Fc polypeptide and a peptide linker.

5. A recombinant vector comprising the nucleic acid molecule of claim 1 that directs the expression of an SVPH1–8 polypeptide encoded by said nucleic acid molecule.

6. An isolated host cell transformed, transfected, or transduced with the recombinant vector of claim 5.

7. A method for the expression of an SVPH1–8 polypeptide having proteinase activity, the method comprising culturing the host cell of claim 6 under conditions promoting expression of said SVPH1–8 polypeptide.

8. The method of claim 7, further comprising recovering the expressed SVPH1–8 polypeptide.

9. An isolated nucleic acid molecule wherein the nucleic acid molecule encodes a polypeptide having disintegrin activity and comprising an amino acid sequence selected from the group consisting of:
   (a) amino acids 27 through 501 of SEQ ID NO:2;
   (b) amino acids 27 through 680 of SEQ ID NO:2;
   (c) amino acids 199 through 501 of SEQ ID NO:2; and
   (d) amino acids 199 through 680 of SEQ ID NO:2.

10. An isolated nucleic acid molecule encoding a fusion protein and comprising the nucleotide sequence of the nucleic acid of claim 9, wherein said nucleic acid molecule encoding a fusion protein further comprises a nucleotide sequence encoding a polypeptide selected from the group consisting of an Fc polypeptide and a peptide linker.

11. A recombinant vector comprising the nucleic acid of claim 9 that directs the expression of an SVPH1–8 polypeptide encoded by said nucleic acid.

12. An isolated host cell transformed, transfected, or transduced with the recombinant vector of claim 11.

13. A method for the expression of an SVPH1–8 polypeptide having disintegrin activity, the method comprising culturing the host cell of claim 12 under conditions promoting expression of said SVPH1–8 polypeptide.

14. The method of claim 13, further comprising recovering the expressed SVPH1–8 polypeptide.

* * * * *

SEQUENCE LISTING

```
<160> NUMBER OF SEQ ID NOS: 2

<210> SEQ ID NO 1
<211> LENGTH: 2169
<212> TYPE: DNA
<213> ORGANISM: Homo sapiens

<400> SEQUENCE: 1
atggcagtgg atgggaccct cgtgtacatc agggtcactc ttctgctgct ctggcttggg      60 gtattttttgt ctatttccgg ctactgtcag gctgggccct cccagcattt cacttccccg    120
gaagtggtga tccccttgaa ggtgatcagc aggggcagaa gtgcaaaggc tcctggatgg    180
ctctcctata gtctgcggtt tggggggccag aaacacgttg ttcatatgag ggtcaagaag    240
ctcttagttt ctagacacct cccagtgttc acctacacag atgagcgtgc actcctggag    300
gatcagctct tcatcccaga tgactgttac tatcatggtt acgtggaggg tgcccctgag    360
tctctggttg tgttcagtgc ttgttttggg ggctttcgag gagtattaaa aataagtggc    420
ctcacttatg aaattgaacc catcaggcac tctgccacat ttgaacacct ggtttacaaa    480
gtaaacagta atgagacaca attcccagct atgagatgtg gcttaacaga gaaggaagta    540
gcacgccaac agttggaatt tgaagaggct gagaactcag ctctggaacc aaaatctgct    600
ggtgactggt ggactcatgc atggtttctg gagctagttg ttgtggtgaa ccatgatttc    660
ttcatttact ctcaaagcaa catctcaaag gtgcaagagg atgtatttct tgttgtcaac    720
atagtggatt ccatgtatca gcagttaggt acttacataa ttttgattgg aattgaaatt    780
tggaatcaag gaaatgtttt cccaatgaca agcatagaac aggtcctgaa cgatttctct    840
caatggaaac aaatcagtct ttcccagcta cagcatgatg ctgcacatat gttcataaaa    900
aattcactta taagtatact tggcctagcc tatgttgcag gaatatgtcg tccacctatt    960
gattgtggag ttgataattt tcaaggagat acctggtctc tttttgccaa cactgtggcc   1020
catgagttag gtcatacgtt gggtatgcag catgatgaag aattctgttt ttgtggggaa   1080
agaggttgca tcatgaatac ttttagagtg ccagcagaga aattccaccaa ttgcagttac   1140
```

-continued

```
gctgatttta tgaagaccac cttaaaccag ggatcatgtc tgcataatcc tccaagattg   1200
ggggaaatct ttatgctaaa gcgctgtggg aatggtgtgg ttgaaagaga agagcagtgt   1260
gactgtggat ccgtacagca gtgtgaacaa gacgcctgtt gtctgttgaa ctgcactcta   1320
aggcctgggg ctgcctgtgc ttttgggctt tgttgcaaag actgcaagtt catgccatca   1380
ggggaactct gtagacaaga ggtcaatgaa tgtgaccttc cagaatggtg caatggaaca   1440
tctcatcagt gtccagaaga tagatatgtg caggacggga tccctgtag tgacagtgcc    1500 tactgctatc aaaagaggtg taataaccat gaccagcatt gcagggagat ttttggtaaa   1560
gatgcaaaaa gtgcatctca gaattgctat aaagaaatca actctcaggg aaaccgtttt   1620
ggtcactgtg gtataaatgg cacaacatac ctaaatgtc atatctctga tgtcttttgt    1680
gggagagttc aatgtgagaa tgtgagagac attcctcttc tccaagatca ttttactttg   1740
cagcacactc atatcaatgg tgtcacctgc tggggtattg actatcattt aaggatgaac   1800
atatctgaca ttggtgaagt gaaagatggt actgtgtgtg cccaggaaa gatctgcatc    1860 cataagaagt gtgtcagtct gtctgtcttg tcacatgtct gccttcctga gacctgcaat   1920
atgaagggga tctgcaataa caaacatcac tgccactgtg gctatgggtg gtccccaccc   1980
tactgccagc acagaggcta tggggggcagt attgacagtg gcccagcatc tgcaaagaga   2040 ggagttttt tgccgctgat tgtgattcct tctttgtctg ttttgacttt cctgtttact    2100
gtcgggcttc ttatgtatct acgacaatgt tctggtccca agaaactaa ggctcattca    2160 tcaggttaa                                                          2169
```

<210> SEQ ID NO 2
<211> LENGTH: 722
<212> TYPE: PRT
<213> ORGANISM: Homo sapiens

<400> SEQUENCE: 2

```
Met Ala Val Asp Gly Thr Leu Val Tyr Ile Arg Val Thr Leu Leu Leu
 1               5                  10                  15

Leu Trp Leu Gly Val Phe Leu Ser Ile Ser Gly Tyr Cys Gln Ala Gly
            20                  25                  30

Pro Ser Gln His Phe Thr Ser Pro Glu Val Val Ile Pro Leu Lys Val
        35                  40                  45

Ile Ser Arg Gly Arg Ser Ala Lys Ala Pro Gly Trp Leu Ser Tyr Ser
    50                  55                  60

Leu Arg Phe Gly Gly Gln Lys His Val Val His Met Arg Val Lys Lys
65                  70                  75                  80

Leu Leu Val Ser Arg His Leu Pro Val Phe Thr Tyr Thr Asp Glu Arg
                85                  90                  95

Ala Leu Leu Glu Asp Gln Leu Phe Ile Pro Asp Asp Cys Tyr Tyr His
            100                 105                 110

Gly Tyr Val Glu Gly Ala Pro Glu Ser Leu Val Val Phe Ser Ala Cys
        115                 120                 125

Phe Gly Gly Phe Arg Gly Val Leu Lys Ile Ser Gly Leu Thr Tyr Glu
    130                 135                 140

Ile Glu Pro Ile Arg His Ser Ala Thr Phe Glu His Leu Val Tyr Lys
145                 150                 155                 160

Val Asn Ser Asn Glu Thr Gln Phe Pro Ala Met Arg Cys Gly Leu Thr
                165                 170                 175

Glu Lys Glu Val Ala Arg Gln Gln Leu Glu Phe Glu Glu Ala Glu Asn
            180                 185                 190
```

-continued

```
Ser Ala Leu Glu Pro Lys Ser Ala Gly Asp Trp Trp Thr His Ala Trp
        195                 200                 205
Phe Leu Glu Leu Val Val Val Asn His Asp Phe Phe Ile Tyr Ser
        210                 215                 220
Gln Ser Asn Ile Ser Lys Val Gln Glu Asp Val Phe Leu Val Val Asn
225                 230                 235                 240
Ile Val Asp Ser Met Tyr Gln Gln Leu Gly Thr Tyr Ile Ile Leu Ile
                245                 250                 255
Gly Ile Glu Ile Trp Asn Gln Gly Asn Val Phe Pro Met Thr Ser Ile
            260                 265                 270
Glu Gln Val Leu Asn Asp Phe Ser Gln Trp Lys Gln Ile Ser Leu Ser
        275                 280                 285
Gln Leu Gln His Asp Ala Ala His Met Phe Ile Lys Asn Ser Leu Ile
        290                 295                 300
Ser Ile Leu Gly Leu Ala Tyr Val Ala Gly Ile Cys Arg Pro Pro Ile
305                 310                 315                 320
Asp Cys Gly Val Asp Asn Phe Gln Gly Asp Thr Trp Ser Leu Phe Ala
                325                 330                 335
Asn Thr Val Ala His Glu Leu Gly His Thr Leu Gly Met Gln His Asp
            340                 345                 350
Glu Glu Phe Cys Phe Cys Gly Glu Arg Gly Cys Ile Met Asn Thr Phe
        355                 360                 365
Arg Val Pro Ala Glu Lys Phe Thr Asn Cys Ser Tyr Ala Asp Phe Met
        370                 375                 380
Lys Thr Thr Leu Asn Gln Gly Ser Cys Leu His Asn Pro Pro Arg Leu
385                 390                 395                 400
Gly Glu Ile Phe Met Leu Lys Arg Cys Gly Asn Gly Val Val Glu Arg
                405                 410                 415
Glu Glu Gln Cys Asp Cys Gly Ser Val Gln Gln Cys Glu Gln Asp Ala
            420                 425                 430
Cys Cys Leu Leu Asn Cys Thr Leu Arg Pro Gly Ala Ala Cys Ala Phe
        435                 440                 445
Gly Leu Cys Cys Lys Asp Cys Lys Phe Met Pro Ser Gly Glu Leu Cys
        450                 455                 460
Arg Gln Glu Val Asn Glu Cys Asp Leu Pro Glu Trp Cys Asn Gly Thr
465                 470                 475                 480
Ser His Gln Cys Pro Glu Asp Arg Tyr Val Gln Asp Gly Ile Pro Cys
                485                 490                 495
Ser Asp Ser Ala Tyr Cys Tyr Gln Lys Arg Cys Asn Asn His Asp Gln
            500                 505                 510
His Cys Arg Glu Ile Phe Gly Lys Asp Ala Lys Ser Ala Ser Gln Asn
        515                 520                 525
Cys Tyr Lys Glu Ile Asn Ser Gln Gly Asn Arg Phe Gly His Cys Gly
        530                 535                 540
Ile Asn Gly Thr Thr Tyr Leu Lys Cys His Ile Ser Asp Val Phe Cys
545                 550                 555                 560
Gly Arg Val Gln Cys Glu Asn Val Arg Asp Ile Pro Leu Leu Gln Asp
                565                 570                 575
His Phe Thr Leu Gln His Thr His Ile Asn Gly Val Thr Cys Trp Gly
            580                 585                 590
Ile Asp Tyr His Leu Arg Met Asn Ile Ser Asp Ile Gly Glu Val Lys
        595                 600                 605
```

-continued

```
Asp Gly Thr Val Cys Gly Pro Gly Lys Ile Cys Ile His Lys Lys Cys
            610             615             620

Val Ser Leu Ser Val Leu Ser His Val Cys Leu Pro Glu Thr Cys Asn
625                 630             635                     640

Met Lys Gly Ile Cys Asn Asn Lys His His Cys His Cys Gly Tyr Gly
                645             650                     655

Trp Ser Pro Pro Tyr Cys Gln His Arg Gly Tyr Gly Gly Ser Ile Asp
            660             665             670

Ser Gly Pro Ala Ser Ala Lys Arg Gly Val Phe Leu Pro Leu Ile Val
        675             680             685

Ile Pro Ser Leu Ser Val Leu Thr Phe Leu Phe Thr Val Gly Leu Leu
    690             695             700

Met Tyr Leu Arg Gln Cys Ser Gly Pro Lys Glu Thr Lys Ala His Ser
705             710             715                     720

Ser Gly
```